US010246682B2

(12) United States Patent
Clegg et al.

(10) Patent No.: US 10,246,682 B2
(45) Date of Patent: *Apr. 2, 2019

(54) METHODS OF CULTURING RETINAL PIGMENTED EPITHELIUM CELLS, INCLUDING XENO-FREE PRODUCTION, RPE ENRICHMENT, AND CRYOPRESERVATION

(71) Applicant: The Regents of the University of California, Oakland, CA (US)

(72) Inventors: Dennis Clegg, Ventura, CA (US); Sherry T. Hikita, Santa Barbara, CA (US); Lincoln V. Johnson, Santa Barbara, CA (US); Liane Miller, San Francisco, CA (US); Marlene Tsie, Santa Barbara, CA (US); Chelsea D. Presbrey, Flagstaff, AZ (US); Lisa R. Conti, Goleta, CA (US); Michelle A. Maloney, Santa Barbara, CA (US); David R. Hinton, Venice Beach, CA (US); Qirui Hu, Santa Barbara, CA (US)

(73) Assignees: The Regents of the University of California, Oakland, CA (US); University of Southern California, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/816,912

(22) Filed: Nov. 17, 2017

(65) Prior Publication Data

US 2018/0087029 A1 Mar. 29, 2018

Related U.S. Application Data

(63) Continuation of application No. 13/756,489, filed on Jan. 31, 2013, now Pat. No. 9,850,463.

(60) Provisional application No. 61/593,849, filed on Feb. 1, 2012.

(51) Int. Cl.
| | |
|---|---|
| *C12N 5/02* | (2006.01) |
| *C12N 5/00* | (2006.01) |
| *C12N 5/10* | (2006.01) |
| *C12N 5/071* | (2010.01) |
| *C12N 15/00* | (2006.01) |
| *C12N 5/079* | (2010.01) |

(52) U.S. Cl.
CPC ........ *C12N 5/0621* (2013.01); *C12N 2500/98* (2013.01); *C12N 2501/115* (2013.01); *C12N 2501/15* (2013.01); *C12N 2506/02* (2013.01)

(58) Field of Classification Search
CPC .................................................. C12N 5/0621
USPC ....................................................... 435/377
See application file for complete search history.

(56) References Cited

U.S. PATENT DOCUMENTS

| 8,071,373 B2 | 12/2011 | Warren |
| 8,080,416 B2 | 12/2011 | Warren |
| 2012/0009159 A1 | 1/2012 | Humayun et al. |
| 2013/0149284 A1* | 6/2013 | Malcuit ................. A61K 35/12 424/93.7 |

OTHER PUBLICATIONS

Carr et al., "Protective Effects of Human iPS-Derived Retinal Pigment Epithelium Cell Transplantation in the Retinal Dystrophic Rat," PloS One 4(12):e8152 (2009).
Buchholz et al., "Derivation of Functional Retinal Pigmented Epithelium from Induced Pluripotent Stem Cells," Stem Cells 27:2427-2434 (2009).
Carr et al., "Molecular Characterization and functional analysis of phagocytosis by human embryonic stem cell-derived RPE cells using a novel human retinal assay," Mol Vis 15:28 (Jan. 2009).
Klimanskaya et al., "Derivation and Comparative Assessment of Retinal Pigment Epithelium from Human Embryonic Stem Cells Using Transcriptomics," Clon Stem Cells 6:217 (2004).
Haruta et al., "In Vitro and In Vivo Characterization of Pigment Epithelial Cells Differentiated from Primate Embryonic Stem Cells," IVOS 45:1020-1045 (2004).
Swistowski et al., "Xeno-Free Defined Conditions for Culture of Human Embryonic Stem Cells, Neural Stem Cells and Dopaminergic Neurons Derived from Them," Open Access, 2009, PLOS One, vol. 4, Issue 7, pp. 1-11.
Corning, "Corning Synthemax II-SC Substrate for Stem Cell Research to be Unveiled,", Jun. 8, 2012, pp. 1-2.
Rajala et al., "A Defined and Xeno-Free Culture Method Enabling the Establishment of Clinical-Grade Human Embryonic, Induced Pluripotenet and Adipose Stem Cells," Open Access PLOS One, vol. 5, Issue 4, pp. 1-14. 2010.
Melkoumian et al., "Synthetic Peptide-Acrylate Surfaces for Long-Term Self-Renewal and Cardiomyocyte Differentiation of Human Embryonic Stem Cells," 2010 Nature Biotechnology, 28:606-610.
Gamm, "A Novel Serum-Free Method for Culturing Human Prenatal Retinal Pigment Epithelial Cells," !IOVS, Feb. 2008, vol. 49, No. 2, 49:788-799.
Fan et al., "Production of Human Pluripotent Stem Cell Therapeutics under Defined Xeno-free Conditions: Progress and Challenges," stem Cell Rev and Rep (2015) 11-L96-109.
Roobrouck et al., "Differentiation Potential of Human Postnatal Mesenchymal Stem Cells, Mesoangiioblasts, and Multipotent Adult Progenitor Cells Reflected in Their Transcriptome and Partially Influenced by the Culture Conditions," Stem Cells 2011; 29-871-882.

(Continued)

*Primary Examiner* — Valarie E Bertoglio
(74) *Attorney, Agent, or Firm* — Kilpatrick Townsend & Stockton LLP

(57) ABSTRACT

The production of high quality retinal pigmented epithelium (RPE) cells is necessary for research and potential therapeutic uses. Especially desirable are methods for the production of RPE cells using xeno-free culture conditions. Disclosed herein are novel methods for the production of RPE cells from pluripotent cells with high yields, including xeno-free production methods. Also provided are methods of efficiently isolating RPE cells from cultures containing heterogeneous cell types, allowing for substantially pure RPE cell cultures to be established. Additionally, novel methods for the cryopreservation of RPE cells are provided.

19 Claims, 1 Drawing Sheet
(1 of 1 Drawing Sheet(s) Filed in Color)

(56) References Cited

OTHER PUBLICATIONS

NIH (Stem Cell's: Scientific Progress and Future Research Directions), Department of Health and Human Services, Chapter 1, pp. 1-4, Jun. 2001.
Valamehr et al., "Developing Defined Culture Systems for Human Pluripotent Stem Cells," Regen Med. Sep. 2011; 6(5): doi:10.2217/rme.11-54.
Hughes et al., "Proteomic Analysis of Extracellular Matrices Used in Stem Cell Culture," Proteomics 2011, 11, 3983-3991.
Liu, eet al., "Folic Acid Supplementation Stimulates Notch Signaling and Cell Proliferation in Embryonic Neural Stem Cells," J. Clin. Biochem. Nutr., 47, 174-180, Sep. 2010.
Weber et al., Corning Synthemax Surface: a Tool for Feeder-Free Xeno-Free Culture of Human Embryonic Stem Cells, Nature Methods, Dec. 2010; an6-an7.
Klimanskaya, I., "Retinal Pigment Epithelium," Methods in Enzymology, Differentiation of Embryonic Stem Cells, vol. 418, Chapter 11, pp. 169-194, 2006.

* cited by examiner

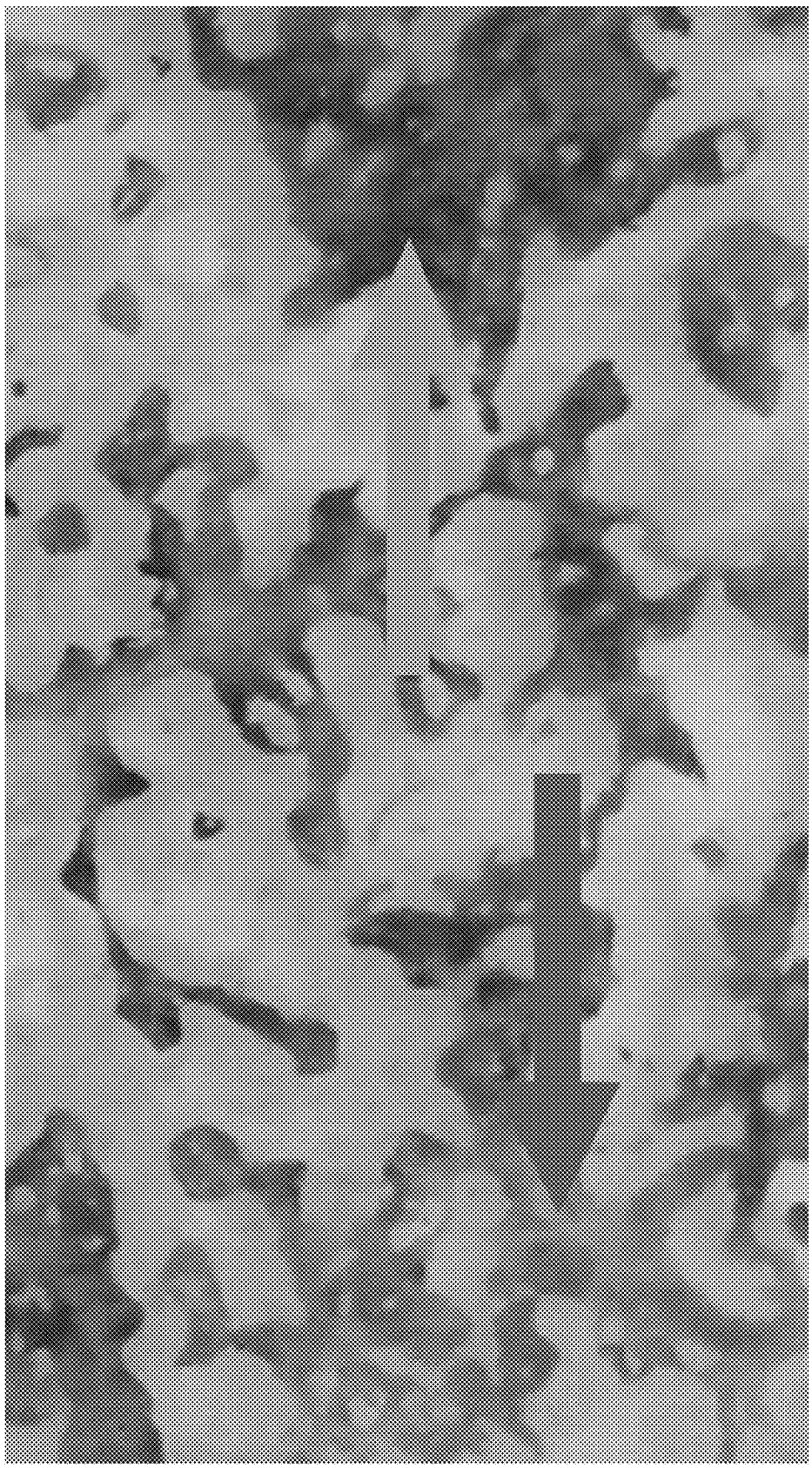

METHODS OF CULTURING RETINAL PIGMENTED EPITHELIUM CELLS, INCLUDING XENO-FREE PRODUCTION, RPE ENRICHMENT, AND CRYOPRESERVATION

CROSS-REFERENCE TO RELATED APPLICATIONS

This application claims the benefit of and is a continuation application of U.S. patent application Ser. No. 13/756,489, filed on Jan. 31, 2013 (U.S. Pat. No. 9,850,463, issued Dec. 26, 2017), which claims priority to U.S. Provisional Patent Application Ser. No. 61/593,849, filed on Feb. 1, 2012, and the contents of both cited applications are herein incorporated by reference in their entirety.

STATEMENT REGARDING FEDERALLY SPONSORED RESEARCH OR DEVELOPMENT

Not applicable.

REFERENCE TO SEQUENCE LISTING, A TABLE, OR A COMPUTER PROGRAM LISTING COMPACT DISK APPENDIX

Not applicable.

BACKGROUND OF THE INVENTION

The retinal pigmented epithelium (RPE) is a layer of cells in the eye. The RPE is adjacent, on one side, to the sensory retina cells which perceive light and transmit visual information to the optic nerve. On the other side of the RPE is the choroid tissue, a vascularized region which supplies the overlying cells of the eye with water, nutrients and other compounds. The RPE plays many critical roles in maintaining vision including isolating the tissues of the eye from the general circulatory system, maintaining the proper ionic environment, processing discarded outer photoreceptor elements from the photoreceptor cells of the neural retina, and protecting the retina from excess light. RPE cells form a flat mosaic of hexagonal cells tightly bound at their junctions.

Various conditions may result in damage and dysfunction of the RPE cells. For example, in some forms of retinitis pigmentosa, RPE cells exhibit abnormalities and dysfunction that affect vision. Another example is age-related macular degeneration (AMD), a disease that gradually diminishes vision in the macula, or central region of the eye. AMD is a leading cause of vision loss in persons 60 years of age and older. It is estimated that in the United States 30% of people over age 75 suffer from some form of AMD. There are few therapies available for AMD and none that effectively cure or reverse the condition. In some forms of AMD, deposits of cellular debris (drusen) form between the RPE and the underlying nourishing choroid, leading to death and dysfunction of the RPE cells. Choroidal neovascularization (CNV) is an AMD subtype characterized by abnormal blood vessel proliferation of the choroidal tissue and the resultant loss of vision resulting from damage to the overlying retinal cells. Geographic atrophy is another form of AMD characterized by atrophy of the retinal pigmented epithelial cells and the resultant death of the overlying retinal cells.

It has been demonstrated, both in animals and in human patients, that transplantation of healthy RPE cells to damaged or destroyed regions can aid in restoring vision (see daCruz et al., RPE transplantation and its role in retinal disease, Progress in Retinal and Eye Research 26:598-635 (2007)). For example, in patients with CNV, surgery to remove the heavily vascularized tissue followed by transplant of RPE cells from the patients' own eyes was shown to restore vision (see Chen, et al., Long-term visual and microperimetry outcomes following autologous retinal pigment epithelium choroid graft for neovascular age-related macular degeneration, Clinical and Experimental Ophthalmology 37:275-285 (2009)).

To maximize therapeutic potential, it would be advantageous to obtain large supplies of high quality RPE cells for transplant purposes. RPE cells derived from stem cells and induced pluripotent cells present a potential source of abundant and potentially immune-compatible RPE tissues for transplant. For example, RPE cells derived from induced pluripotent stem cells have been created and transplanted in rats and were shown to be functional (see Carr et al., Protective Effects of Human iPS-Derived Retinal Pigment Epithelium Cell Transplantation in the Retinal Dystrophic Rat, PloS One 4(12):e8152 (2009)).

The derivation of RPE cells from pluripotent cells has been demonstrated previously, for example, see Buchholz et al., Derivation of Functional Retinal Pigmented Epithelium from Induced Pluripotent Stem Cells, Stem Cells 27:2427-2434 (2009) and Carr et al., Molecular Characterization and functional analysis of phagocytosis by human embryonic stem cell-derived RPE cells using a novel human retinal assay, Mol Vis 15:283-295 (2009). However, prior art methods of deriving RPE cells from pluripotent cells suffer from low yields. There is a need in the art for facile, high yielding and highly consistent methods of creating viable RPE cells from pluripotent cells.

Pluripotent cells are typically cultured on animal-derived substrates, such as mouse feeder cells and they are often cultured in media containing animal-derived proteins and other growth factors. The therapeutic use of RPE tissues derived from pluripotent cells will require animal-free (also called "xeno-free") methods of generating such cells to remove the threat of transmitting viruses, prions, and other pathogenic factors that may be found in animal-derived culture substrates and media. To date, there is no known method of producing RPE cells that is completely free of animal-derived substrates or media. Accordingly, there is a need in the art for xeno-free methods of creating RPE cells from pluripotent cells. There is also a need in the art for the xeno-free, or near xeno-free production of RPE cells from pluripotent cells wherein such methods produce high yields of high quality RPE cells.

SUMMARY OF THE INVENTION

Disclosed herein are novel methods of producing high-quality RPE cells with very high yields. Also disclosed herein are methods of producing RPE cells in near-xeno free conditions and in totally xeno-free conditions for the production of cells that may be used in research, veterinary, and human therapeutic applications. Additionally, the present disclosure teaches new methods of deriving substantially pure cultures of RPE cells from heterogeneous cell cultures by the efficient isolation of substantially pure RPE fractions. Finally, the present disclosure also provides methods of cryopreserving cultured RPE cells.

BRIEF DESCRIPTION OF THE FIGURE

The patent or application file contains at least one color photograph. Copies of this patent or patent application publication with the color photograph will be provided by the Office upon request and payment of the necessary fee.

FIG. 1 is a photograph of a portion of a well of a standard six-well cell culture plate. In this well, differentiation of cultured H9 human embryonic stem cells was initiated by direct transition from MTESR®-1 medium to growth factor-free X-VIVO® 10 medium. Following removal of growth factors, cells were allowed to differentiate for 120 days. A dark brown pigmented region, indicative of differentiation into the RPE phenotype (indicated by the green arrow), contrasts with a lighter, more translucent brown region (indicated by the red arrow). In subsequent RPE enrichment steps using dissociation agents, only the dark brown regions (considered mature RPE) are retained and further propagated.

DETAILED DESCRIPTION OF THE INVENTION

For purposes of this disclosure, the term "RPE cells" refers to any cells having a native pigmented retinal epithelial cell phenotype, including both native cells as well as pigmented retinal epithelial phenotype cells derived from pluripotent cell sources. Such cultured cells have a genetic expression profile similar to that of native RPE cells and assume the polygonal, planar sheet morphology of native RPE cells when grown to confluence on a planar substrate. RPE cells exhibit dark brown pigmentation.

For purposes of this disclosure, "RPE precursor" means a cell having a partial native pigmented retinal epithelial cell phenotype, for example a differentiating cell exhibiting light pigmentation and some of the biological and morphological markers of mature RPE cells, but lacking other biological and morphological markers of the RPE phenotype. RPE precursors exhibit light brown pigmentation.

For purposes of this disclosure, "xeno-free" means having no xenogeneic products of non-human animal origin, such as cells, tissues and/or body fluids, or any tissue or blood components, such as serum, which contain variable and undefined factors. Xeno-free media and culture substrates are made up of known or "defined" components, which reduces the risk of viral contamination, prion transmission, and the batch-to-batch variability that is present using undefined media. Accordingly, xeno-free media and substrates nay contain recombinantly-produced proteins or peptides produced from non-human animal-derived DNA sequences, as such components are of known composition.

The invention encompasses the use of any pluripotent cell. Pluripotent cells are cells that can self-renew and proliferate while remaining in an undifferentiated state and that can, under the proper conditions, be induced to differentiate into specialized cell types, including RPE cells. The term "pluripotent cell" includes stem cells, such as embryonic stem cells ("ESC's") and other types of stem cells, including fetal, amnionic, or somatic stem cells. Exemplary human stem cell lines include the H9 human embryonic stem cell line. Additional exemplary stem cell lines include those made available through the National Institutes of Health Human Embryonic Stem Cell Registry and the Howard Hughes Medical Institute HUES collection (as described in Cowan, C. A. et. al, Derivation of Embryonic Stem-cell Lines from Human Blastocysts. New England Journal of Medicine. 350; 13. (2004)).

The term "pluripotent cell" also encompasses induced pluripotent stem cells. Induced pluripotent stem cells, sometimes abbreviated "iPS cells" or "iPSC's" are a type of pluripotent stem cell which has been derived from a non-pluripotent cell, such as a somatic cell that has been reprogrammed to induce a pluripotent, undifferentiated phenotype by various means. iPS cells can be created by inducing the expression of certain regulatory genes or by the exogenous application of certain proteins. Methods for the induction of iPS cells are known in the art and include, for example, the methods described in Zhou et al., Adenoviral gene delivery can reprogram human fibroblasts to induced pluripotent stem cells, Stem Cells 27 (11): 2667-74 (2009), Huangfu et al., Induction of pluripotent stem cells by defined factors is greatly improved by small-molecule compounds, Nature Biotechnology 26 (7): 795(2008), Woltjen et al., piggyBac transposition reprograms fibroblasts to induced pluripotent stem cells, Nature 458 (7239): 766-770 (2009), and Zhou et al., Generation of Induced Pluripotent Stem Cells Using Recombinant Proteins, Cell Stem Cell 8:381-384 (2009).

The invention encompasses the use of pluripotent cells from any species, including human, murine, porcine, canine, feline, rattus, and other mammal species. Cells derived through the use of the invention may be applied in any research or therapeutic use, including medical and veterinary uses.

Growth Media.

Pluripotent cells are grown and maintained in growth media, a solution of salts, sugars, amino acids and growth factors. For those embodiments of the invention which do not require xeno-free conditions, such as the pigmented cell enrichment or cryopreservation methods described below, the invention encompasses the use any growth medium which supports the growth and maintenance of pluripotent cells and cultured RPE cells derived from pluripotent cells. Exemplary media include that described in Klimanskaya et al., Derivation and Comparative Assessment of Retinal Pigment Epithelium from Human Embryonic Stem Cells Using Transcriptomics, Cloning and Stem Cells 6:217 (2004), the medium described in Carr et al., Molecular Characterization and functional analysis of phagocytosis by human embryonic stem cell-derived RPE cells using a novel human retinal assay, Mol Vis 15:283-295 (2009), and other culture media known in the art to support the growth and maintenance of pluripotent cells and cultured RPE cells.

Exemplary commercially available xeno-free media include X-VIVO® 10 media (Lonza Biosciences), X-VIVO® 15 media (Lonza Biosciences), MTESR®-2 media (Stem Cell Technologies), NUTRISTEM® media (StemGent) and HESCGRO™ media (Millipore). Lonza X-VIVO® 10 media supplemented with 5-40% Xeno-Free KNOCKOUT® Serum Replacement (XF-KOSR, Invitrogen) or a similar xeno-free serum replacement may also be used. Additional examples of xeno-free culture media include that described in Rajala et al., A Defined and Xeno-Free Culture Method Enabling the Establishment of Clinical-Grade Human Embryonic, Induced Pluripotent and Adipose Stem Cells, PloS ONE 5:e10246 (2010), the medium described in Swistowski et al., Xeno-Free Defined Conditions for Culture of Human Embryonic Stem Cells, Neural Stem Cells and Dopaminergic Neurons Derived from Them, PLoS ONE 4: e6233 (2009), and the medium described in Amit et al., Feeder layer- and serum-free culture of human embryonic stem cells, Biology of Reproduction 70:837 (2004). Additionally, the media described in Thompson et al., Embryonic Stem Cell Lines Derived from Human Blastocysts, Science 282:1145 (1998) or the media described by the WiCell web site may be modified by the replacement of fetal bovine serum or standard KOSR (KNOCKOUT® serum replacement) with Xeno-Free KNOCKOUT® Serum Replacement (XF-KOSR, Invitrogen) or a like xeno-free KOSR substitute. The growth medium described in U.S. Pat. No. 5,945,337, Method for Culturing CD34 Cells in a Serum-Free Medium, by Brown et al. may also be utilized.

Another xeno-free medium that may be used is MX-302. MX-302 is composed of Iscove's Modified Dulbecco's Medium (IMDM) (as described in Iscove, N. N., Guilbert, L. J. and Weyman, C. (1980). Complete Replacement of Serum in Primary Cultures of Erythropoietin Dependent Red Cell Precursors [CFU-E] by Albumin, Transferrin, Iron, Unsaturated Fatty Acid, Lecithin and Cholesterol. Exp. Cell Research. 126, 121-126) supplemented with B-27™ Serum-free Supplement (Invitrogen). For example, 495 ml of IMDM may be combined with 5 ml of 0.5×B-27™ to make a half liter of MX-302. B-27™ may be substituted with similar supplements, such as NTS-21 or B-18 supplement (as described in Brewer G J, Cotman C W (1989) Survival and growth of hippocampal neurons in defined medium at low density: advantages of a sandwich culture technique at low oxygen. Brain Res 494:65-74).

Another xeno-free media that may be used in the methods of the invention is Essential 8, or "E8," as described in Chen et al., Chemically defined conditions for human iPSC derivation and culture, Nature Methods 8:424-9 (2011).

Culture Substrates.

For those embodiments of the invention which do not require xeno-free conditions, the invention encompasses the use of any substrate which supports the growth of pluripotent cells, as well as the growth of differentiated cultured RPE cells, including commonly-used substrates such as Matrigel™ or mouse embryonic fibroblast feed cell layers, as known in the art.

For xeno-free culture methods, disclosed herein is a method which avoids the use of technically challenging human feeder cell layers such as human embryonic fibroblasts, fallopian tube epithelium, or foreskin fibroblasts. The xeno-free embodiments of the invention can employ any culture substrate which is substantially free of animal-derived serum, proteins, or other factors and which supports the growth and maintenance of pluripotent cells and cultured RPE cells derived from pluripotent cells. Exemplary substrates include commercially available substrates, such as SYNTHEMAX® substrate (Corning Life Sciences), SYNTHEMAX® II-SC substrate (Corning Life Sciences), CELLSTART™ substrate (Invitrogen), GELSTART™ substrate (Invitrogen), and STEMADHERE™ substrate (Primorigen).

Additionally, human vitronectin, purified from human plasma or produced by recombinant expression, may serve as a xeno-free substrate for pluripotent cell growth, for example as described in Braam et al., Recombinant Vitronectin Is a Functionally Defined Substrate That Supports Human Embryonic Stem Cell Self-Renewal via αVβ5 Integrin, Stem Cells 26:2257-2265 (2008). Human-derived recombinant Laminin, for example Laminin 511 (BD) or Laminin 521 (Biolamina) may be utilized. Additionally, poly-D-lysine may act as a substrate, for example as described in Harb et al., The Rho-Rock-Myosin Signaling Axis Determines Cell-Cell Integrity of Self-Renewing Pluripotent Stem Cells. PLoS ONE 3(8): e3001 (2008).

Various polymer-peptide conjugates may also serve as xeno-free culture substrates. For example, acrylate polymer functionalized with short peptide sequences derived from the vitronectin protein may be utilized. For example, the acrylate-peptide compositions described in Melkoumian et al., Synthetic peptide-acrylate surfaces for long-term self-renewal and cardiomyocyte differentiation of human embryonic stem cells, Nature Biotechnology, 28(6):606-610 (2010) may be utilized. Polymer-peptide cell culture surfaces such as those described in U.S. patent application Ser. No. 12/845,411, Peptide-polymer Cell Culture Articles and Methods of Making, by Martin et al. may also be utilized.

Another polymer-peptide combination that may serve as a xeno-free culture substrate is parylene, coated with vitronectin, laminin, fibronectin, or peptides derived therefrom. For example, parylene-C membranes, for example of 0.3-6.5 um thickness, such as those described in Lu, Semipermeable Parylene Membrane as an Artificial Bruch's Membrane, 16th International Solid State Sensors, Actuators, and Microsystems Conference, 950-953 (2011) or available from MiniPumps LLC (Pasadena, Calif.) may be coated with solubilized vitronectin at about 10 μg/ml in 1×DPBS+CaCl2+MgCl2. The vitronectin solution is allowed to sit on the membrane at room temperature for at least two hours, during which time the parylene membrane becomes coated with adsorbed vitronectin protein. The vitronectin-coated parylene membrane may thereafter be seeded with pluripotent or RPE cells.

Commercial Equivalents.

Some embodiments of the invention are directed to the use of commercially-available products, which are named by their trade names. It is understood that the invention also encompasses the use of functional equivalents of commercially-available products. A functional equivalent of a commercially available product means a composition that is substantially identical to a commercially-provided product in its function, for example, a composition made up of components that are identical, modified, or functional substitutions of the components in a given commercial product, such components being present in substantially identical, modified, or functionally equivalent proportions as the components of the commercial product.

Cell Culture Vessels and Culture Conditions. Pluripotent cells and RPE cells derived from pluripotent cells can be cultured using various vessels and culture conditions. Cells may be grown, maintained, or differentiated in any suitable vessel such as glass, polystyrene, and polycarbonate. The invention encompasses the use of any cell culture system, including 2-dimensional culture, three-dimensional culture, and liquid suspension culture techniques. Two-dimensional culture techniques are preferred for the ease of cell observation and passaging. Vessels of any size may be used, such as T-75 flasks (75 cm$^2$ surface area/flask), 96-well plates (0.32 cm$^2$ surface area/well), 24-well plates (1.9 cm$^2$ surface area/well), or six well plates (9.5 cm$^2$ surface area/well), for example Becton, Dickinson and Company Corp. FALCON® polystyrene plates. Culture vessels can be coated with the desired culture substrate using methods known in the art, including substrate supplier protocols. Alternatively, culture vessels pre-coated with substrates by the manufacturer are available for many types of substrate, for example SYNTHEMAX® substrate coated T-75 flasks (75 cm$^2$ surface area/flask) from Corning Life Sciences. Cell cultures may be maintained at any temperature, with preferred temperatures at or near 37° C. Adequate medium to avoid limiting growth should be added to each vessel, and medium should be changed at regular intervals to avoid depletion of nutrients and accumulation of waste substances. For example, using standard six-well plates (well diameter of 9.5 cm$^2$), about 4 ml of medium should be used per well.

Plating density, when transferring cells between vessels, is expressed as a ratio, for example 1:2, 1:3, etc. This terminology refers to the act of dividing the cellular colony residing in a single vessel and parsing it among two or more vessels of equal or like size. For example, when plating cells 1:2, the cells from a first vessel are divided in half and transplanted to two new vessels of the same size. A plating density of 1:1 means that the cells are not divided, but simply transferred to a fresh vessel.

Maintaining Pluripotency.

When maintaining and expanding pluripotent cells, it is essential that pluripotency of the cells be maintained until differentiation is desired. Pluripotency of stem cells can be maintained by including any known composition, or mixture of compositions, which acts to reduce the percentage of pluripotent cells that commence differentiation and lose their pluripotency. One such composition that maintains pluripotency is basic fibroblast growth factor (bFGF), used, for example, at a concentration in the range of 50-100 µg/ml. A concentration of about 80 µg/ml bFGF is preferred in some embodiments of the invention. Recombinantly produced, animal-free human bFGF is readily available from many suppliers, including, for example, Millipore, Life Technologies, Cell Sciences Products, Peprotech, and others. Alternatively, other agents may be used as bFGF substitutes for example, the synthetic peptide F2A4-K-NS (as described in Lin et al., Synthetic peptide F2A4-K-NS mimics fibroblast growth factor-2 in vitro and is angiogenic in vivo, International Journal of Molecular Medicine 17:833-839 (2006)), trichostatin A (as described in Durcova-Hills et al., Reprogramming Primordial Germ Cells into Pluripotent Stem Cells. PLoS ONE 3(10) (2008)), and other bFGF substitutes known in the art.

Maintenance of pluripotency is also aided by the use of medium supplemented with transforming growth factor β1 (TGF β1), for example at a concentration in the range of 0.1 ng/ml to 1 ng/ml. A concentration at or near 0.5 ng/ml is utilized in some embodiments of the invention. Recombinant human TGF β1 is readily available from a number of commercial suppliers. Alternatively, other agents may be used as TGF β1 substitutes, such as those described in PCT Patent Application Serial Number PCT/US1999/015432, Peptide Compositions Mimicking TGF-Beta Activity, by Bhatnagar et al., and other TGF β1 substitute known in the art.

Even in the presence of bFGF and/or TGF β1, or their substitutes, some subset of cultured cells may commence differentiation, as evidenced by dark spots or pigmentation or by other morphological evidence of differentiation. When passaging undifferentiated cells, these differentiated regions of the cellular mass on the substrate should be excised and discarded, for example, by scalpel.

Transfer to Xeno-Free Conditions. Pluripotent cells may be effectively maintained and propagated using many methods known in the art which are not xeno-free. For example, pluripotent calls may be maintained on a Matrigel™ (BD Biosciences) substrate, in mTeSR-1™ (Stemcell Technologies) medium.

In many cases, cells that have been cultured under conditions which are not xeno-free will be used as the starting material for xeno-free culture. In such cases, it will be necessary to transition the cells to xeno-free conditions, a process that is often stressful to the cells. If the pluripotent cells are being cultured both in non-xeno-free medium and on non-xeno-free substrates, it is recommended that the transition to xeno-free medium and substrate be carried out consecutively rather than simultaneously to minimize cell death. Preferably, the transition to xeno-free medium is carried out first, followed by the transition to xeno-free substrate.

For transition to xeno-free medium, it is recommended that the cells be cultured in a mixture of their current growth medium and the xeno-free medium, wherein the proportion of xeno-free medium increases over time. For example, cells may be passaged at weekly intervals in a series of solutions containing percentage ratios of their initial non xeno-free media to xeno-free media of 25:75, then 50:50, then 75:25, then 0:100. Medium should be changed as necessary to avoid depletion of nutrients and growth factors and to prevent the buildup of toxic waste products. For example, media changing may occur every other day.

Passaging of undifferentiated pluripotent cells during the transition to xeno-free conditions should take place when the cells in each well are at least 70-90% undifferentiated and preferably before 50% spontaneous differentiation is observed. Typically, pluripotent cells will reach 10-50% differentiation at 5-7 days, even when maintained in bFGF, TGF (β1 and/or other compositions which aid in maintaining pluripotency. Plating densities of about 1:1 to 1:4 are recommended at each passage. Considerable cell death may occur during the transition to xeno-free conditions and if this is observed, cells may be seeded at higher density to compensate for this increased mortality. Passage is carried out by manual dissection to remove any differentiated regions and subsequent transfer of the undifferentiated regions to the new vessel. For the final passage to 100% xeno-free medium, cells should be passaged at a density of 1:1 if the plate is <50% confluent and at a density of 1:2 if the cells in the source well or plate are at >50% confluency.

In order to transition to xeno-free substrate, undifferentiated colonies are manually transferred to the xeno-free substrate at a dilution of 1:3 if the well is at >50% confluency and at a dilution of 1:2 if the well is at <50% confluency. Low rates of cell attachment, a decrease in colony size, and increased cell death may be observed during the transition. If a well reaches 50% differentiation, passaging is recommended. Three or more passages may be required for the cells to adjust to the new substrate.

Maintenance and expansion of stem cells. Obtaining high yields of differentiated RPE cells requires an adequate supply of undifferentiated precursors. Once stem cells have been acclimated to xeno-free conditions, cells can be cultured for several passages in order to expand the number of cells. While cells are growing to confluence, medium should be changed frequently, for example, daily, every other day, or every third day. Changing medium every other day is preferred. Cells should be passaged before or just at the time of reaching 100% confluency. Typically, this may be seven to ten days after seeding. Preferably, cells are passaged when they reach 85-100% confluency and less than 50% differentiation has occurred. When passaging, any differentiated regions should be excised from the undifferentiated cells and discarded. For expansion of pluripotent cells, plating densities ranging from 1:3 to 1:6 are preferred.

Initiating Differentiation.

The production of RPE cells commences when the pluripotent cells are allowed to differentiate. Pluripotent cell cultures at any stage may be employed. Advantageously, yields are increased when differentiation is initiated about 4-7 days after undifferentiated cells have been passaged, using cells from culture vessels in which no more than 15-20% of the cells have undergone spontaneous differentiation. In some cases it is advantageous to utilize pluripotent cells which have been passaged at least twice, as it has been observed by the inventors of this disclosure that the use of undifferentiated cells of higher passage number leads to higher yields of RPE cells, and results in RPE cells having more robust pigmentation.

To induce differentiation of pluripotent stem cells, the growth medium is switched to a medium that lacks bFGF, TGF β1, or any other composition used to maintain pluripotency. Thereafter, cells are maintained using such medium, which is changed regularly, for example, three times per week. Upon withdrawal of bFGF and TGF β1, or any other composition used to maintain pluripotency, the cells will start to spontaneously differentiate into various cell lineages, for example, epithelial cells, neuronal cells, muscle cells, and RPE cells. These various cell types tend to form clusters or "rafts" of a single cell type within the culture dish.

During the differentiation process, it is advantageous that the differentiating cells are left in place and are not passaged. In a matter of weeks, within thirty to forty days after initiation of differentiation, pigmentation of RPE cells becomes observable. At first, the pigmentation is very slight. For example, early pigmentation may manifest as a single, very light brown spot about 500 μm in diameter, in each cell, visible to the naked eye. Visualization of pigmented cells can be aided by holding the culture plate over a white surface, such a piece of paper and/or by examination using a microscope. Pigmentation will not typically occur throughout the entire culture vessel, but will be isolated to various regions. This pigmentation will spread and pigmented cells will darken over the next several weeks, up to 120 days from the onset of differentiation.

Dark brown pigmentation will be observed in regions of the differentiating cells. In FIG. 1, a typical region of dark brown pigmented cells is visible (highlighted by a green arrow). The color of the cells is dark brown and the region is mostly opaque. When such dark brown differentiated RPE cells are plated on a planar growth substrate, they will grow in the characteristic single-cell layer flat sheet "mosaic" of polygonal and hexagonal shaped cells that is characteristic of native RPE cells. These cells also express genetic markers of RPE identity found in native RPE cells (assayed as described below). Therefore, these dark brown cells, due to their genetic, morphological and probable functional similarities to their native counterparts, will also be described as RPE cells. Surrounding the region of dark brown cells are regions of non-pigmented cells, and regions of more translucent, lightly pigmented cells (highlighted by a red arrow in FIG. 1). These cells are non-RPE cells or immature RPE precursors and their propagation is not desired.

RPE Cell Enrichment.

New cultures containing high percentages of darkly pigmented RPE cells may be derived from a heterogeneous mass of spontaneously differentiating cells. The new cultures are enriched in RPE cells by the efficient isolation of RPE cells from the heterogeneous cultures. The pigmented RPE cells can be effectively isolated by selective removal of surrounding non-pigmented and lightly pigmented cells, allowing subsequent seeding of substantially pure subcultures of mature RPE cells in new culture vessels. The prior art method of pigmented cell enrichment is to mechanically dissect small regions of darkly pigmented cells from the heterogeneous mass of cells in the culture dish and plate them in new vessels. Disclosed herein is a novel method of enrichment which is more efficient than the prior art technique and which allows for more stringent isolation of the desired RPE cell type.

The enrichment method described below is advantageously applied when the differentiating cells are at about 100-120 days after the initiation of differentiation. It has been observed by the inventors of this disclosure that earlier performance of the isolation process results in lower yields of pigmented cells, and that later enrichment results in cells having lower viability and capacity for re-seeding.

The isolation method is carried out by treating the differentiated cell cultures with an optimal amount of a cell dissociation agent. It has advantageously been discovered by the inventors of the present disclosure that within a culture vessel containing a heterogeneous mass of spontaneously differentiating cells, pigmented RPE cells are more adherent to the culture substrate than other cell types. In other words, non-RPE cells or lightly pigmented RPE precursors are more sensitive to dissociation agents and are thus more easily loosened or removed from the culture substrate. Using this differential sensitivity to cell dissociation agents, non-pigmented cells can be selectively removed from the heterogeneous mass.

Cell dissociation agents include any compound, including enzymes, non-enzymatic peptides and chemical compounds, and blends thereof which are known to effect the dissociation of cells. Cells in culture tend to adhere to each other and to the culture substrate, via various adhesion molecules. Cell dissociation agents are compounds that disrupt or degrade adhesion molecules and break up cellular monolayers and clumps as well as facilitate the removal of cell monolayers and clumps from the underlying substrates.

Various cell dissociation agents are known in the art. Trypsin, a serine protease which cleaves peptide chains is commonly used as a dissociation agent. Trypsin is effective at concentrations ranging from 1.0 mg/ml to 5.0 mg/ml. When dissociating cells, it is important that cells not be in contact with the trypsin for extended periods of time, as the enzyme will hydrolyze cellular proteins and greatly reduce cellular viability. Exposure time to trypsin of six minutes or less is recommended. Trypsin from a variety of sources, including human, porcine, bovine, murine, and others, is readily available from commercial suppliers.

For xeno-free applications, a number of recombinant xeno-free trypsin and trypsin-like enzymes are readily available from commercial suppliers. Exemplary xeno-free trypsin and trypsin-like products include TRYPLE™ enzyme (from Invitrogen), TRYPZEAN® trypsin (from SigmaAldrich), Xeno-Free Trypsin (from Millipore), and animal-origin free trypsin (from Biogenomics).

An exemplary dissociation agent to use in the enzymatic enrichment process is TRYPLE™ enzyme, which may be used, for example, in the range of 50-100% 1× TRYPLE™ enzyme, for example at a concentration of 100% 1× TrypLE™ (i.e. undiluted). When culturing cells in a six-well plate, 1 ml of 1× TRYPLE™ enzyme may be added to each well to effect dissociation. When using TRYPLE™ enzyme, exposure times of 5-30 minutes may be used, for example. However, cell viability is negatively affected by prolonged exposure in excess of six minutes, and exposure times of about five to six minutes are generally more effective for selective loosening and removal of non-pigmented and lightly pigmented cells while maximizing viability.

Another exemplary type of dissociation agent for the enrichment process is collagenase. Collagenases degrade collagen. For example, Cizyme™ Collagenase HA (Vitacyte) can be used in a concentration of about 0.1 mg/ml (0.35 Units/ml), with exposure times of 5-30 minutes. Shorter incubation times in the 5-15 minutes are effective and preserve cell viability better than longer exposure times. Collagenase Type IV (Gibco) may be used in a concentration of 50 to 400 Units per ml, for example at a concentration of about 200 Units/ml. Incubation times with Collagenases Type IV may range from 1-15 minutes, for example, at an exposure time of about five minutes.

The enzyme dipsase, a protease which cleaves fibronectin, collagen IV, and collagen, may also be used in the enrichment process. Dispase is available from a number of suppliers and may be used, for example, at concentrations ranging from 0.01-0.1 mg/ml, for example at a concentration of about 0.05 mg/ml. Exposure times may range from 5-30 minutes, for example with an exposure time of 15 minutes.

Another exemplary dissociation agent for pigmented cell enrichment is Accutase™ (Innovative Cell Technologies). Accutase may be used at a strength of 25-100% (i.e. diluted 1:4, Accutase: buffer to totally undiluted Accutase), with undiluted Accutase, for example, being particularly effective. Exemplary exposure times for Accutase may range from 5-30 minutes, for example. An exposure time of about 10 minutes is effective.

Any buffer known to effect cell dissociation may also be used for pigmented cell enrichment. For example, EDTA at a concentration of 0.1-1.0 mM may be utilized. EDTA at a concentration of about 0.5 mM is effective. Exemplary effective EDTA exposure times range from 5-30 minutes. An exposure time of less than twenty minutes is effective. The buffer Dulbecco's Phosphate Buffered Saline (DPBS) may be utilized, for example at a strength of 100% (i.e. undiluted). Exemplary DPBS exposure times range from 3-30 minutes. An exposure times of five minutes is effective. When using DPBS, vigorous washing is recommended.

Any other cell dissociation agent capable of dissociating cells from each other and from culture surfaces may also be used. For example, SplitCell™ (Midimed) is another enzymatic cell dissociation agent. HyQTase™ (Thermo Scientific) is a plant-derived cell dissociation agent.

Combinations of dissociation agents may be used as well. For example, a combination of Cizyme™ Collagenase HA at a concentration of about 0.1 mg/ml and dispase at a concentration of about 0.5 mg/l may be used. When using this combination, exemplary effective exposure times range from 5-30 minutes. An exposure time of 15 minutes is effective.

For each of the dissociation agents described above, the preferred coverage is in the range of 0.1-0.4 ml per cm2 of culture vessel area. For example, when using a standard six well plate (9.5 cm2 surface area/well), about 1 ml of enzyme solution may be added to effect enrichment.

The pigmented cell enrichment process is carried out by applying an effective amount of a cell dissociation agent to the culture vessel, for an effective exposure period. An "effective concentration" of cell dissociation agent is a concentration that, when applied to a culture vessel containing a heterogeneous mix of differentiating cells including pigmented RPE cells for a given period of time, will cause the loosening and/or removal of non-pigmented differentiating cells and lightly pigmented immature RPE cells from the culture substrate while leaving a substantial proportion of darkly pigmented RPE cells more firmly adhered to the culture substrate than the non-pigmented cells and immature RPE cells. An "effective exposure time" means, for a given dissociation agent at a given concentration, an exposure period during which non-pigmented and lightly pigmented cells are loosened or removed from the culture substrate while a substantial proportion of darkly pigmented RPE cells remain viable and more firmly adhered to the culture substrate than non-pigmented cells. One skilled in the art can readily determine effective cell dissociation agent concentrations and effective cell dissociation agent exposure times by assaying the selected dissociation agent (or blend of dissociation agents) at a range of concentrations and exposure times and observing which combinations of concentration and exposure time facilitate facile removal of non-pigmented cells and lightly pigmented cells while leaving darkly pigmented RPE cells substantially attached to the culture substrate, while maintaining the viability of a substantial portion of the darkly pigmented cells. Sub-optimal concentrations of dissociation agent and/or sub-optimal exposure times will not effectively loosen or remove non-pigmented cells and lightly pigmented immature RPE cells. Supra-optimal concentrations of dissociation agent and/or supra-optimal exposure times will result in loosening and removal of darkly pigmented cells in addition to undesirable cells. In general, shorter effective exposure times are preferred, since supra-optimal times will decrease cell viability and lower the yields of viable RPE cells.

After applying an effective concentration of cell dissociation agent solution for an effective exposure period, physical disruption of non-pigmented and lightly pigmented cells will aid in their removal. Darkly pigmented, nearly opaque regions of the culture substrate, which are patches or "rafts" of RPE cells will be discernible, surrounded by non-pigmented and more lightly pigmented, more translucent regions of non-RPE cells and/or immature RPE cells. The regions highlighted by the green and red arrows in FIG. 1 depict a typical darkly pigmented region (green arrow) and a typical more translucent, lightly pigmented region (red arrow). It is the darkly pigmented regions that are to be retained while removal of the non-pigmented and lightly pigmented regions is desired. Physical disruption may be performed using a cell scraper, pipette tip, scalpel, or other instrument, or washing, rinsing, and/or agitation. When using an instrument, disruption is effectively performed by placing the instrument at the border of a raft of darkly pigmented cells and scraping outward, facilitating the removal of non-pigmented and lightly pigmented cells.

After an effective exposure time to the dissociation agent, the dissociation agent solution should be quickly removed and rinsed away, or diluted (for example, 10× with buffer) and then removed to avoid exposure times beyond the optimal time interval. Cell dissociation solution is removed, for example by pipetting, and the dissociated non-pigmented cells and lightly pigmented will be removed in this solution. After removal of the cell dissociation agent and the suspended non-pigmented cells and lightly pigmented contained in it, the remaining cells, enriched in darkly pigmented RPE cells, can be washed with buffer, for example DPBS, to aid in the removal of any remaining loose non-pigmented and lightly pigmented cells.

Optionally, an additional mechanical removal step can be performed following the removal of the dissociation agent solution and/or buffer wash, by replenishing the vessel with medium, absent any cell dissociation agent. Any remaining non-pigmented and lightly pigmented cells, loosened by the previous exposure to cell dissociation agents, can be worked with pipette tips, cell scrapers, or other instruments to physically dislodge them from the culture substrate. This process can take place over a time period of several minutes, for example from five to ten minutes. The additional mechanical removal step is completed by removal of the medium, along with dislodged non-pigmented and lightly pigmented cells, for example by pipetting. Subsequent to medium removal, the cells may be washed with buffer, for example, DPBS to further aid in the removal of loosened cells.

Optionally, a second dissociation agent treatment step for the removal of non-pigmented and lightly pigmented cells may be performed by repeating the entire process described above. In short, in this embodiment, the cells are treated with a solution containing a dissociation agent, during which time the non-pigmented and lightly pigmented cells are worked mechanically to promote their removal from the substrate surface. The dissociation agent is then removed or diluted, followed by optional buffer wash and/or mechanical working. Then a second exposure to a solution containing a dissociation agent is performed, along with mechanical loosening of undesired cell types during the period of exposure to the dissociation agent. The dissociation agent is then removed, optionally followed by a buffer wash and/or additional mechanical treatment of undesired unpigmented or lightly pigmented cells in medium. Performing a second dissociation agent treatment step has been found to increase the yield and purity of isolated darkly pigmented RPE cells. If the dissociation agent treatment step is repeated, it is generally preferable to shorten the exposure time in at least one of the treatment steps (relative to the exposure time utilized in a single dissociation agent step) to avoid cumulative supra-optimal exposure times which may negatively impact cell viability or which may cause premature dissociation of darkly pigmented RPE cells. For example, a first exposure to the dissociation agent of one to three minutes, for example, two minutes, followed by a second exposure of 5-15 minutes may be performed, for example using undiluted TRYPLE™ enzyme.

Dissociation of RPE Cells.

Once the culture vessels have been enriched in darkly pigmented RPE cells by removal of non-pigmented and lightly pigmented cells, the darkly pigmented cells can be removed and subcultured in new vessels for the continued growth and expansion of substantially pure cultures of RPE cells. Removal of the darkly pigmented cells from the culture substrate may be accomplished immediately after removal of undesired cell types as described above, or the darkly pigmented cells may be left in media for a short time (for example, from a few hours to overnight) before their removal from the substrate. To remove darkly pigmented cells, a cell dissociation agent is added to the vessel in an effective concentration for an effective time to promote the detachment of pigmented cells from the culture substrate. In general, the dissociation agents described above, at the same concentrations and exposure times utilized for the removal of non-pigmented cells, may be used in this step. Because previous exposure to the dissociation agent(s) has slightly loosened the darkly pigmented cells, a second exposure to the same dissociation agent for the same incubation time will generally be adequate for facilitating removal of the darkly pigmented RPE cells from the culture substrate. In some cases, lesser concentrations and shorter exposure times will be sufficient, especially when the substrate has optionally been exposed to two previous incubations in dissociation agent solution, as described in the embodiment above. In the case of especially adherent darkly pigmented cells, it may be necessary to increase the concentration of the dissociation agent and to lengthen the exposure time, relative to the concentration and exposure time used in the first part of the enrichment process. Upon completion of the dissociation agent incubation period, cell viability is improved if the dissociation agent is promptly removed and residual agent rinsed away, or is significantly diluted and then removed.

Exemplary dissociation agents for removing the RPE cells from the culture substrate include TRYPLE™ enzyme which can be diluted with buffer, for example at a ratio of 1:4 TRYPLE™ enzyme to buffer, or which may be applied undiluted. Undiluted TRYPLE™ enzyme is effective. TRYPLE™ enzyme incubation times of five to fifteen minutes may be used. Exposure times of five to ten minutes are effective, though times of 5-6 minutes are generally more desirable to increase cell viability. ACCUTASE® solution, for example, diluted 1:4 with buffer or undiluted may be used. ACCUTASE® solution exposure times of five to thirty minutes may be used. Another exemplary dissociation agent is trypsin (for example, Recombinant Trypsin/EDTA from Cascade Biologics/Invitrogen Cell Culture or TRYPZEAN® Solution from Sigma-Aldrich) which may be used in concentrations ranging from 25-100%, with exposure times ranging from 5-30 minutes. For each of the dissociation agents and exemplary concentrations described above, the preferred coverage is in the range of 0.01-0.4 ml per $cm^2$ of culture vessel area. For example, when using a standard six well plate (9.5 $cm^2$ surface area/well), about 1 ml of dissociation agent solution may be added to effect enrichment.

After incubation in the dissociation agent, the darkly pigmented RPE cells can be gently dislodged from the culture substrate by use of a cell scraper or other instrument. Next, the solution in the culture vessel, containing cell dissociation agent, can be circulated, agitated, or otherwise put in motion to effect further removal of attached darkly pigmented cells and to promote dissociation of darkly pigmented cell clumps and rafts into single cells and smaller aggregates. For example, the cell dissociation agent solution may be triturated, i.e. repeatedly drawn into and expelled from a pipette. For example, the solution may be triturated twenty to thirty times, over a period of one to two minutes. The aspiration and expulsion from the pipette should be performed slowly, without the creation of bubbles, in order to reduce the degree of mechanical stress imposed on the cells.

Detachment and trituration will yield a cell suspension containing small darkly pigmented cell aggregates and single darkly pigmented cells. This cell suspension should be transferred to a centrifuge tube of culture medium in order to dilute the cell dissociation agent. For example, one ml of cell suspension can be added to nine ml of medium. The diluted cell suspension is then centrifuged, for example at 173×g for five minutes. After centrifugation, the supernatant is removed and a pellet containing pigmented cells is recovered and resuspended in medium. The pellet is resuspended by agitation, for example gentle trituration with a pipette.

Next, the resuspended cell suspension is passed through a filter to remove cell clumps and other debris, yielding a suspension substantially composed of single darkly pigmented RPE cells. For example, a 40 µm cell strainer may be utilized. Trituration and washing of the bottom of the filter will increase the yield of single cells.

RPE Cell Quantification and Seeding.

Optimal cell seeding is promoted by quantifying the number of darkly pigmented RPE cells captured in the previous steps. The volume of the filtered cell suspension is recorded. Thereafter, samples of the cell suspension may be analyzed to determine the concentration of cells. Cells can be quantified by any number of means, including cell counters, hemacytometers, and other cell quantification methods known in the art, to determine the concentration of RPE cells in the suspension. Additional analyses may be performed to determine the proportion of RPE cells vs. non-RPE cells in the suspension, and to quantify the proportion of viable to dead cells.

Cells can be counted in a cell counter. For example, a cell counter with gating diameter set between 6 and 20 µm may be used. Cells may also be counted and analyzed in a hemacytometer. For example, trypan blue or other cell viability assays known in the art may be used to determine cell viability percentages. In a hemacytometer, the trypan blue assay is aided by observing the cells under brightfield conditions without phase filter. The hemacytometer may also be used to quantify the percentage of non-pigmented cells. This is best achieved by viewing samples in the absence of trypan blue, under phase filters.

Once the cell suspension has been analyzed to determine the concentration of viable RPE cells, the cell suspension can be appropriately diluted for optimal cell seeding. Seeding densities ranging from 57,000 to 300,000 viable RPE cells per cm2 substrate may be used. The proper dilution to achieve this optimal density is determined using the size of the culture vessel to be used, the concentration of cells in the suspension, the proportion of RPE cells in the suspension to non-RPE cells, and the percentage of viable RPE cells in the suspension.

Properly diluted cell suspension is then distributed in culture vessels. Lateral sliding of the culture vessel in a star-like pattern or plate rocking may be used to evenly distribute the cells across the vessel. Medium should be changed the day after passage and bi-weekly thereafter. Cells generally reach confluence within 4 days and should be passaged every thirty days. When plating diluted cell suspensions, antibiotics such as Normocin may be used in the media to prevent contamination. If used, antibiotics should be omitted 7 days following passage.

Characterization of Cultured RPE Cells.

In order to be suitable for therapeutic transplant and other functions, the cultured RPE cells must be functionally similar to native RPE cells. Similarity to native RPE can be assessed by several different means, including genetic profiling methods and functional assays.

Several genes act as markers of RPE cell identity, being preferentially expressed in native RPE cells. Exemplary gene markers confirming RPE phenotype include integrin alpha-V (Itgav), Cd36, Cd81, Lactadferin (Mfge8), Growth-arrest specific 6 (Gas6), focal adhesion kinase (Fak), Protein S (Pros1), Cathespin D (Ctsd), Clathrin light chain a, clathrin light chain b, clathrin light chain c, proto-oncogene tyrosine-protein kinase Mer (Mertk), Retinal pigment epithelium-specific 65 kDa protein (RPE65), lecithin retinol acyltransferase (LRAT), Luteinizing hormone receptor mRNA binding protein (RLBP1), Tyrosinase (TYR), melanocyte protein PMEL 17 (SILV), microphthalima-associated transcription factor (MITF), pigment epithelium-derived factor (PEDF), keratin type 1 cytoskeletal 8 (KRT8), and cellular retinaldehyde-binding protein (CRALBP).

Genetic markers can be confirmed by various methods known in the art, such as quantifying marker gene mRNA or quantifying marker gene protein gene products, for example by immunoassay. Additional RPE genetic markers and methods of assaying therefore are described in Carr et al., Molecular Characterization and functional analysis of phagocytosis by human embryonic stem cell-derived RPE cells using a novel human retinal assay, Mol Vis 15:283-295 (2009), Liao et al., Molecular signature of primary retinal pigment epithelium and stem-cell-derived RPE cells, Human Molecular Genetics 19: 4229-4238 (2010), and Klimanskaya et al., Derivation and Comparative Assessment of Retinal Pigment Epithelium from Human Embryonic Stem Cells Using Transcriptomics, Cloning and Stem Cells 6:217 (2004).

One function of native RPE cells is to aid in the renewal of rod cells. Rod cells are rod-shaped photoreceptor cells in the eye that are renewed by adding new segments at the base of the rod structure and shedding the oldest segments at the distal end of the rod structure. In normal RPE cell function, RPE cells phagocytose shed rod outer segments (ROS), preventing their accumulation. Failure to phagocytose is detrimental to photoreceptor cell function. Established assays to measure the ability of cultured putative RPE cells to phagocytose ROS are described in detail in Carr et al., Molecular Characterization and functional analysis of phagocytosis by human embryonic stem cell-derived RPE cells using a novel human retinal assay, Mol Vis 15:283-295 (2009), Klimanskaya et al., Derivation and Comparative Assessment of Retinal Pigment Epithelium from Human Embryonic Stem Cells Using Transcriptomics, Cloning and Stem Cells 6:217 (2004), and Haruta et al., In Vitro and In Vivo Characterization of Pigment Epithelial Cells Differentiated from Primate Embryonic Stem Cells, IVOS 45:1020-1045 (2004).

Further growth and uses of RPE cells. As described above, seeded pigmented RPE cells derived using the methods described herein will grow to confluency. These cells may be further passaged multiple times. However, it has been observed by the inventors of the present disclosure that following reseeding from the enrichment step, after five passages, the cultured RPE cells begin to lose their RPE-like characteristics and they begin to assume a more fibroblast-like morphology. Therefore, for therapeutic uses, it is generally advantageous that cells are passaged no more than three times after enrichment before transplant and/or other therapeutic uses, to insure the cells maintain a strong native RPE phenotype.

Cryopreservation of Cultured RPE Cells.

Cultured RPE cells may be cryopreserved, which advantageously allows long term storage. It is recommended that cultured RPE cells be cryopreserved when they are at about 80-95% confluence, as it has been found that cells at this stage have greater viability and higher retention of RPE pigment and morphology upon thaw.

The cryopreservation process is initiated by first removing the cells from the culture substrate by exposing the cultured RPE cells to dissociation agents, and then gently dislodging them from the substrate with an instrument such as a cell scraper. Any dissociation agent may be utilized, for example those described above in the RPE cell enrichment process, at similar concentrations and for similar exposure times. For example, RPE cells may be removed from the substrate with the aid of trypsin, TRYPLE™ enzyme, VERSENE® agent, or ACCUTASE® solution, for example at concentrations of 10-30% enzyme (the ratio of 1× enzyme solution volume to medium volume) or at concentrations of 0.01 to 0.1 ml enzyme solution per $cm^2$ of substrate, for example at a concentration of about 0.1 ml enzyme solution per $cm^2$ substrate. For example, if adding TRYPLE™ enzyme to standard six-well plates (9.5 $cm^2$) containing 4 ml medium per well, the addition of 1 ml of 1× TRYPLE™ enzyme will be effective. Exposure times of five to seven minutes are effective in loosening cells from the substrate. Using a cell scraper or other instrument, cells can then be gently lifted off the substrate. The contents of the culture vessel may then be agitated, for example, gently triturated with a pipette, for a period of ten to twenty seconds to create a cell suspension. Advantageously, following trituration, the cell suspension is then diluted to halt the action of dissociation agents, for example by a 1:10 dilution with medium or buffer. The diluted suspension is then centrifuged, for example, at 1,000 rpm for five minutes. The pellet is then resuspended in medium and filtered, for example with a 35 µm or 40 µm filter cap.

An effective concentration of cells in cryopreservation solution is about 250,000 to 500,000 viable pigmented RPE cells per 0.5-1.0 ml of cryopreservative. To determine the proper dilution, after filtering, small aliquots of the filtered cell suspension can be characterized as described above to determine the proportion of living cells and the proportion of RPE cells to non-RPE cells. Once these parameters are established, the number of live RPE cells per unit volume in the resuspension can be determined and the optimal amount of cryopreservative can be used. The cells suspension is then centrifuged, for example, at 1,000 rpm for five minutes, and the cell pellet is then resuspended in the proper amount of cryopreservative.

Any cryopreservative known in the art may be used. Exemplary xeno-free cryopreservatives include CryoSTOR10™ (Biological Industries), CryoSTEM™ (BioLife Solutions), and Kryolife™ (LifeLine Cell Technology). A serum-free (but not xeno-free) cryopreservative is mFreSR™ (Stem Cell Technologies).

Cells in cryopreservative, in appropriate cryovials, placed in an appropriate freezing container, for example Mr. Frosty™ (Thermo Scientific), can then be placed in −80° C. conditions for 8-12 hours. Optionally, the freezing container can be first placed in −20 C conditions for two hours, then moved to −80° C., which increases viability upon thaw. After −80° C. freezing, the freezing container is then placed in liquid nitrogen for long-term storage.

To thaw the cells, the contents of the cryovials are thawed, for example, by placing the cryovial in a warm water bath and allowing the contents to melt. It has been observed that best results are attained if the contents of the cryovial are allowed to melt until just a small chip of ice remains. Then the thawed contents of the cryovial are then added to warm medium, for example 9 mls. This solution is then centrifuged, for example at 1,000 rpm for five minutes, and the cellular pellet is resuspended in medium, for example 1-2 mls.

Small aliquots of the resuspended cells may then be characterized, as described above to determine the proportion of pigmented and viable cells. Based on these parameters, proper dilution can be performed for subsequent cell seeding on culture substrate at densities such as 57,000 to 300,000 cells per square centimeter. Cells generally reach confluence within 4 days and should be passaged every thirty days. Medium should be changed the day after passage and bi-weekly thereafter.

EXAMPLES

Example 1. Exemplary Protocol for the Transition of Pluripotent Cells from Non-Xeno-Free Culture Conditions to Xeno-Free Culture Conditions This exemplary protocol describes the transition of pluripotent human embryonic stem cells cultured (hESC's) under non-xeno conditions to fully xeno-free culture conditions. The starting materials are hESC's grown on MATRIGEL® substrate (BD Biosciences) (murine-derived protein mix) culture substrate, in MTESR®-1 (StemCell Technologies) growth media, which contains bovine-derived BSA. The xeno free media in this Example is X-VIVO® 10 media and the xeno-free substrate is SYNTHEMAX® substrate.

Pluripotent cells are transitioned into new medium and onto new substrate consecutively. In this protocol, cell survival and viability is enhanced by transitioning cells into xeno-free medium gradually, over a period of passages, which takes about 4 weeks.

All passages are performed by manual dissection. All culture media contain 50 µg/ml Normocin to minimize chance of contamination in long-term experiments. Use of 100 µg/ml Normocin is not recommended for culture of undifferentiated hESC's because they exhibit increased cell death. For a 6-well plate, the total volume of medium used in each well is about 4 ml/well.

Percent differentiation can be used as a gauge of adaptation. Total colony and differentiated colony counts are performed from a minimum of 3 wells. Counts are averaged and percentage differentiation (average number of differentiated colonies/average number of total colonies×100) is calculated. This is performed just prior to each passage and for at least 3 subsequent passages after complete transition into xeno-free conditions.

The cells may need some time (3 to 4 passages) to adjust to the 100% xeno-free medium conditions. Considerable cell death may be observed during this period. Seeding at higher density during this time is suggested. After full transition to 100% xeno-free medium and substrate, performing karyotype analysis to confirm RPE phenotype is recommended.

Transition Passage 1:

Starting with cells maintained in MTESR®-1 medium on MATRIGEL® substrate in 6-well plates, undifferentiated colonies are passaged 1:3 via manual dissection into a 6-well plate that contains 75% MTESR®-1 medium and 25% X-VIVO® 10 medium, the X-VIVO® 10 medium being supplemented with 80 ng/ml human bFGF and 0.5 ng/ml TGFβ1 (Note: throughout protocol the addition of human bFGF and TGFβ1 only applies to the volume of X-VIVO® 10 medium and NOT to the volume of MTESR®-1 medium). Medium is replaced every other day with 75% MTESR®-1 medium and 25% X-VIVO® 10 medium+80 ng/ml human bFGF+0.5 ng/ml TGFβ1 until the next passage (approximately 5-7 days).

Transition Passage 2:

Cells are passaged when each well is 10-30% differentiated and preferably before each well exhibits >50% differentiation. Undifferentiated colonies are manually dissected, for example mechanically removed from the substrate using a cell scraper or excised by scalpel, and are passaged 1:3 into 50% MTESR®-1 medium and 50% X-VIVO® 10 medium supplemented with 80 ng/ml human bFGF and 0.5 ng/ml TGFβ1 on MATRIGEL® substrate in a 6-well plate. Medium is replaced every other day with 50% MTESR®-1 medium and 50% X-VIVO® 10 medium+80 ng/ml human bFGF+0.5 ng/ml TGFβ1 until the next passage (approximately 5-7 days).

Transition Passage 3:

Cells are passaged when each well is 10-30% differentiated and preferably before each well exhibits >50% differentiation. Undifferentiated colonies are manually dissected and passaged 1:3 onto MATRIGEL® substrate in a 6-well plate, in a solution of 25% MTESR®-1 medium and 75% X-VIVO® 10 medium supplemented with 80 ng/ml human bFGF and 0.5 ng/ml TGFβ1 on. Medium is replaced every other day with 25% MTESR®-1 medium and 75% X-VIVO® 10 medium+80 ng/ml human bFGF+0.5 ng/ml TGFβ1 until the next passage (approximately 5-7 days).

Transition Passage 4:

Cells are passaged when each well is 10-30% differentiated and preferably before each well exhibits >50% differentiation. Cells are passaged 1:2 or even 1:1, depending on confluency of each well. If a well is <50% confluent, cells are plated at 1:1, if >50% confluent, cells are plated 1:2. There is typically more cell death and less attachment at this and subsequent passages. Undifferentiated colonies are passaged via manual dissection into a solution of 100% X-VIVO® 10 medium+80 ng/ml human bFGF+0.5 ng/ml TGFβ1 on MATRIGEL® substrate in a 6-well plate. This medium is replaced every other day. The cells typically show a change in percent differentiation/well and the colonies may require passaging more or less frequently than previously.

Once the cells are transitioned to xeno-free media, the cells are transitioned to a xeno-free substrate. One ml/well of 37° C. X-VIVO® 10 media is added to a 6-well SYNTHEMAX® plate. Undifferentiated colonies are manually passaged from a MATRIGEL® substrate to the SYNTHEMAX® plate 1:2 or 1:3 depending on confluency. If each well is >50% confluency, undifferentiated colonies are plated at 1:3, and if a well is at <50% confluence, undifferentiated colonies are plated are plated at 1:2.

Medium is replaced every other day and cells are observed closely for an increase in percent differentiation. Fewer cells may attach and colony size may decrease during the transition from the MATRIGEL® substrate to the SYNTHEMAX® plate. Increased cell death may also be noted. If cells in a single well exceed 50% differentiation, they are passaged earlier (3-5 days). Three or more passages may be required for the cells to adjust to the new substrate.

Alternative protocol: Direct transition into xeno-free medium, from MTESR®-1 media to X-VIVO® 10 media. Transition Passage 1: Starting with cells maintained in MTESR®-1 media on a MATRIGEL® substrate in 6-well plates, allow undifferentiated colonies to reach 60 to 90% confluence then replace the medium with 100% X-VIVO® 10 media without growth factors.

The materials and tools described in this exemplary protocol are for illustration purposes only. It is understood that similar and/or equivalent materials and tools may be used, and that slight modifications of the steps performed, or the order of the steps performed may be made. For example, other xeno-free media and substrates, as described herein, may be used in place of a SYNTHEMAX® substrate and X-VIVO® 10 media.

Example 2. Culture and RPE Differentiation from Human Embryonic Stem Cells

This Example describes an exemplary protocol for the culture and differentiation of hESC's on a SYNTHEMAX® substrate, with X-VIVO® 10 media.

All passages of undifferentiated hESC are performed by manual dissection. Note that culture and differentiation media contain 50 µg/ml NORMOCIN™ reagent to minimize chance of contamination in long term experiments. Use of 100 µg/ml NORMOCIN™ reagent is not recommended for culture of undifferentiated hESC's because they exhibit increased cell death. A 6-well plate format is used for all culture procedures using a total volume of 4 ml medium per well. For aid in identifying differentiated vs. undifferentiated hESC colonies, reference to pages 5-7 of Human Stem Cell Manual A Laboratory Guide, Eds: Loring, J. F., Wesselschmidt, R. L., and Schwartz, P. H. (2007) may be made.

Undifferentiated hESC's are maintained on substrate-coated 6-well plates in X-VIVO® 10 medium containing 80 ng/ml human bFGF, 0.5 ng/ml TGFβ1, and 50 µg/ml NORMOCIN™ reagent. Medium is replaced every other day until cultures are ready for passage. Undifferentiated hESC cultures are expanded by passaging once they reach 85-100% confluence and before 50% differentiation occurs, at a split ratio of 1:3 to 1:6.

To induce RPE cell differentiation, the culture medium is replaced with X-VIVO® 10 medium+50 µg/ml NORMOCIN™ reagent that has not been supplemented with bFGF or TGFβ1. (Note: This change is made using cultures at 85-100% confluence with >50% differentiation, typically 7-10 days following seeding of the hESC).

Medium is replaced 3 times weekly (e.g. Mon., Wed., Fri.) using unsupplemented X-VIVO® 10 medium+50 µg/ml NORMOCIN™ reagent and cells are monitored for pigmentation. Pigmentation onset generally occurs by day 30 following change to unsupplemented X-VIVO® 10 medium+50 µg/ml NORMOCIN™ reagent and should be observed by day 40. Observation of pigmentation onset is aided by holding the plate over a white piece of paper or the sleeve of a white lab coat. Pigmentation onset may be observed as a single very small (500 µm in diameter) very light brown spot in each cell undergoing pigmentation. The pigmentation should expand and continue to darken up to 120 days.

Once pigmentation within a well reaches at least 50% dark brown (for example, as depicted in the region in FIG. 1 indicated by the green arrow, dark pigmented cells may be isolated for the creation of cultures enriched in dark pigmented cells, following the RPE enrichment protocol described in Example 4 below. Wells that do not attain 50% pigmentation after 120 days of culture in unsupplemented X-VIVO® 10 medium should not be utilized for RPE cell enrichment.

The materials and tools described in this exemplary protocol are for illustration purposes only. It is understood that similar and/or equivalent materials and tools may be used, and that slight modifications of the steps performed, or the order of the steps performed may be made. For example, other xeno-free media and substrates, as described herein, may be used in place of a SYNTHEMAX® substrate and X-VIVO® 10 media. Other xeno-free substrates and media, as described herein, may be used.

Example 3. Derivation of RPE Cells from Pluripotent Cells Under Xeno-Free Culture Conditions Using methods based on the exemplary protocol described in Example 2, RPE cells were produced under xeno-free culture conditions. H9 human embryonic stem cells were plated in two wells of a standard six-well plate coated with SYNTHEMAX® media. The H9 cells were cultured in X-VIVO® 10 medium supplemented with 80 ng/ml human bFGF+0.5 ng/ml TGFβ1. After two passages, six wells of undifferentiated H9 cells were present. When the cells reached 85-95% confluence, the growth medium was changed to a X-VIVO® 10 medium without growth factors. Spontaneous differentiation of the plated cells commenced.

At 120 days after the initiation of differentiation, the wells contained darkly pigmented cells, with coverage of the darkly pigmented cells in the range of 15-60% of the substrate area. Darkly pigmented cells exhibited RPE physical morphology. Darkly pigmented cells were excised and assayed for markers of RPE phenotype, including RPE65, RLBP1, Best1, MITF isoform 2, Silver/PMEL, TYRP1, and PEDF. The markers were present at levels which confirmed the RPE phenotype of the darkly pigmented cells.

Similar experiments were performed using other xeno-free substrates, including CELLSTART™ substrate and human laminin 511, in X-VIVO® 10 medium or other xeno-free media, including DMEM/F12 supplemented with xeno-free serum replacement and bFGF and TGFB1, and TeSR™ 2 (a xeno-free version of MTESR®-1). Successful production of darkly pigmented cells displaying RPE morphology and RPE marker expression was observed in all experiments, with varying yields.

Example 4. Exemplary RPE Enrichment Protocol

In this Example, a protocol is described for the derivation of cell cultures enriched in darkly pigmented RPE cells from a mass of heterogeneous, spontaneously differentiating cells. The dissociation agent used in this exemplary protocol is TRYPLE™ enzyme by Invitrogen.

Six-well plates are coated with substrate. The RPE cell enrichment protocol uses medium supplemented with 100 µg/ml NORMOCIN™ reagent because of the time and frequency with which the plates are open. About 25 ml X-VIVO® 10+100 µg/ml NORMOCIN™ reagent is warmed in a 37° C. water bath or each well to be enriched. DPBS (~10 ml per well) is aliquoted and warmed in a 37° C. water bath. TRYPLE™ enzyme (2 ml per well), typically stored at 4° C., is brought to room temperature just before the enrichment procedure and used undiluted, as supplied by the manufacturer.

A dissecting hood is stocked with sterile P10 pipette tips and pipette tip holder (e.g. weighted dental tool with tapered handle or P10 pipettor or similar). Spent media is aspirated from each well of the culture plate, and each well is washed twice with 2 ml DPBS per well. One ml TRYPLE™ enzyme is then added to each well. Immediately thereafter, removal of non-pigmented and lightly pigmented cells is commenced. The culture plate is placed on the 37° C. heated stage of a dissecting microscope in a dissecting hood and the plate lid is removed. A P10 pipette tip or other instrument is used to detach as many lightly-pigmented and non-pigmented regions as possible by placing the tip of the pipette at the edge of a darkly pigmented (RPE cell) region and moving it away, disrupting the surrounding non-pigmented and lightly pigmented cells. Some non-pigmented regions may separate with little pressure. Other areas may remain attached despite manipulation. If darkly pigmented areas become loose and begin to tear, disruption should be halted and resumed in another region. The total time of exposure to TRYPLE™ enzyme should not exceed 6 minutes. After 5 minutes of the detachment procedure, the lid of the culture plate is replaced and the plate is returned to the tissue culture hood. If enriching multiple wells, it is recommended that the procedure be staggered to ensure that each well is exposed for no more than 6 minutes. After this initial "picking-to-remove step" with enzyme, the heat plate can be turned off.

The TRYPLE™ enzyme solution containing detached non-pigmented and lightly pigmented cells is removed and discarded and 2 ml X-VIVO® 10 media supplemented with 100 µg/ml NORMOCIN™ reagent medium is added to each well, and the plate is returned to the dissecting scope for additional detachment of non-pigmented and lightly-pigmented cells (5 to 10 min per well). If much debris persists, medium is replaced, and the wells may be washed with DPBS between media change. After the picking-to-remove step is complete, medium is replaced with 4 ml per well X-VIVO® 10 media supplemented with 100 µg/ml NORMOCIN™ reagent. Dissociating and seeding may be performed at this point, or the culture plates may be stored at 37° C. overnight for harvesting the next day.

Dissociation and Seeding: Wells are washed with 2 ml DPBS twice. The buffer is then aspirated and 1 ml TRYPLE™ enzyme is added per well. The plates are incubated at 37° C. for 5 minutes in the cell culture incubator. During the incubation, tubes are prepared for collecting the cell suspension (For example, for each well: 9 ml X-VIVO® 10 media supplemented with 100 µg/ml NORMOCIN™ reagent in a 15 ml conical tube). The darkly pigmented RPE cells are gently dislodged with a cell scraper while the TRYPLE™ solution is still present. The contents of each well are triturated with a P1000 pipettor set to 1000 µL about 15 times or until the liquid is dark. Some clumps will remain. The liquid should be aspirated and dispensed gently, taking care to avoid bubbles.

For each well from the previous step, the cell suspension (about 1 ml) is transferred to a conical 15 ml tube containing 9 ml X-VIVO® 10 media supplemented with 100 µg/ml NORMOCIN™ reagent. The cell suspension is spun at room temperature in a benchtop centrifuge at 173 g (1,000 RPM in IEC Centra CL2 Centrifuge with Rotor 236 for 15 ml conical tubes) for 5 minutes. The supernatant is removed and discarded, leaving the pellet intact.

The pellet is resuspended in a volume of X-VIVO® 10 media supplemented with 100 µg/ml NORMOCIN™ reagent that is equal to the number of wells (1 ml per well) from the starting plate(s). The pellet is resuspended by gently pipetting up and down several times using a 5 ml serological pipette or a P1000 pipettor set to 1000 µl.

The cell suspension is passed through a 40 µm cell strainer into a 50 ml conical collection tube. If there are many clumps the strainer may clog. To facilitate flow, the solution can be pipetted up and down while scraping the bottom of the strainer with a P1000 tip attached to a pipettor. Care should be taken to scrape gently as the strainer can tear. To ensure most of the cell suspension is collected, the strainer is removed and the P1000 is used to withdraw the suspension from the underside region of the strainer, depositing the collected volume into the 50 ml conical collection tube. The final volume collected after cells have passed through the strainer should be recorded for later calculation of total cells available for plating.

Twenty µl samples of the cell suspension are withdrawn and diluted 10-fold by adding 180 µl of medium or DPBS. The mixture is placed into 1.5 ml microcentrifuge tubes.

Cell concentration is counted using a Millipore Scepter handheld cell counter with the gating diameter set between 6 µm to 20 µm (or to exclude debris, which may appear as a distinct peak below 10 µm). Another option for counting cells is by using a hemacytometer. The hemacytometer counts can facilitate total cell counts, viable cell counts as well as pigmented cell counts. For total cell counts and pigmented versus non-pigmented cell counts, 10 µl of sample is assayed in the absence of trypan blue. To attain a viability count, the cell suspension is diluted two-fold using trypan blue solution (10 µl cell suspension+10 µl trypan blue). For both cell counts, live and total cell counts are best observed using the microscopes phase filter, whereas pigmented and dead/blue cells are best noted under brightfield (by removing the phase filter).

Based on the cell count, the proper volume of cell suspension may be calculated for seeding new substrate-coated culture vessels at a density of 57,000 to 300,000 cells/cm$^2$. For example: for a 6-well plate, 540,000 cells/well are seeded and cultured in a volume of 4 ml X-VIVO® 10 medium supplemented with 100 µg/ml NORMOCIN™ reagent per well. For a T25 flask, 4,275,000 cells are seeded in a total volume of 10 ml X-VIVO® 10 medium supplemented with 100 µg/ml NORMOCIN™ reagent. Plates are placed in a 37° C. incubator, and the plates are slid using a brisk motion in a star-like pattern or a repetitive rocking motion to evenly distribute cells for attachment. Medium is changed 24 hours later. Wells are washed with 2 ml medium to remove debris and pigment granules, if necessary. Medium is replaced twice weekly thereafter. Seven days following passage, NORMOCIN™ reagent is omitted from the medium.

The materials and tools described in this exemplary protocol are for illustration purposes only. It is understood that similar and/or equivalent materials and tools may be used, and that slight modifications of the steps performed, or the order of the steps performed may be made.

Example 5. Derivation of RPE Cell Cultures from Heterogeneous Cultures

Using the methods of the exemplary protocol of Example 4, RPE cells were isolated from a mass of heterogeneous cells and subsequently cultured. Two six-well plates of spontaneously differentiating H9 cells were used. In each well, about 75% of the substrate surface was covered with live cells, of which about ~60% of the surface appeared to be covered with darkly pigmented cells. Enrichment was performed using undiluted TRYPLE™ enzyme. Selective removal of non-RPE cells was performed using a five minute TRYPLE™ enzyme treatment and simultaneous mechanical disruption. Following this, the darkly pigmented cells were dissociated with TRYPLE™ enzyme and added to 120 ml X-VIVO® medium to create a cell suspension that was centrifuged to form a pellet. The cell pellet was resuspended with 12 ml of medium and a cell count was performed. The percentage of live cells in the cell suspension was 89.3%. Based on this live cell count, the darkly pigmented RPE cells were plated in 3×T-75 flasks at a density of 10,000 cells/cm$^2$ culture substrate.

Example 6. Cryopreservation of RPE Cells

In this Example, RPE cells were cryopreserved, thawed, and reseeded, resulting in a high rate of recovery of cells retaining RPE morphology and genotype. The RPE cells used in this example were designated En97, and were derived from H9 embryonic stem cells.

En97 cells were plated on Corning SYNTHEMAX® T75 flasks and grown in X-VIVO® 10 medium until they reached 85-95% confluence. The E97 cells were dissociated and removed from the substrate as follows. TRYPLE™ enzyme (undiluted) was removed from the refrigerator and allowed to come to room temperature. Sterile DPBS and X-VIVO® 10 media (no phenol red, no Gentamicin) were prewarmed in a 37° C. waterbath. Required tools and materials (cell scraper, tubes, P1000 pipettor) were sterilized with 70% ethanol and placed in hood.

Spent medium was aspirated from the T75 flasks and cells were washed twice with warmed DPBS. DPBS was aspirated and 8 mL of TRYPLE™ enzyme was added to each flask for a coverage of about ~0.1 mL/cm$^2$ culture substrate surface. The T75 flasks were placed in an incubator (37° C., 5% CO2) for 2 minutes. TRYPLE™ enzyme was aspirated and 8 mL of fresh TRYPLE™ enzyme was added to the flask, which was then returned to the incubator for 5 minutes. The TRYPLE™ enzyme treated cells were monitored on an inverted microscope to confirm that they were "balling up" and detaching/contracting. Using a cell scraper, the cells were gently removed from the flask. Using a 10 mL pipette, the cell suspension in the flask was gently triturated 5 times until a uniform suspension was attained.

The cells were transferred to a 125 mL sterile media bottle containing 57 mL of warmed X-VIVO® 10 media (this effectively dilutes and inactivates the TRYPLE™ enzyme) for each T75 flask harvested. Each flask was rinsed twice with 8 ml of X-VIVO® 10 medium and the medium was added to the bottle. Total enzyme exposure time was not allowed to exceed 25 minutes.

The cell suspension was divided into two 50 mL conical tubes (40.5 mL/tube) and centrifuged at 173 g (1000 rpm on IEC Centra CL2 centrifuge with Rotor 236) for 5 minutes at room temperature. The supernatant was aspirated and discarded and the cells were resuspended in about 5 ml of warmed X-VIVO® 10 medium per T75 flask harvested. The resuspended cells were filtered through a BD FALCON® 40 μm cell strainer. Ten μl of the cell suspension was removed and assayed with a Hausser Scientific 3100 Hausser Bright Line Hemacytometer, using Trypan blue stain, to attain a count of live, dead, and total cells.

Based on the live cell count, the volume of cryopreservative solution required to resuspend the cells at a concentration of 3×10$^6$ cells/mL was calculated. The cell suspension was centrifuged at 173 g (1000 rpm on IEC Centra CL2 centrifuge with Rotor 236) for 5 minutes at room temperature. The supernatant was aspirated and discarded and the pellet was resuspended in ~2.5 mL Cryostor 10™ cryopreservative (BioLife Solutions) by gentle trituration using a pipettor. The resulting cell suspension was then transferred to Corning 1.2 mL Cryogenic Vials (1 ml per vial). The cryovials were then placed into a Nalgene Mr. Frosty™ Cryo Freezing Container and placed in a −80° C freezer overnight. The next day, the cryovials were transferred to liquid nitrogen, and stored for up to 12 months.

Thawing and plating of cryopreserved RPE cells. The day of thaw, BD FALCON® 6-well culture plates were coated with MATRIGEL® substrate. One ml of X-VIVO® 10 medium was placed in each well and the plates were incubated until the time of seeding.

A single cryovial was removed from the liquid nitrogen and immersed in a 37° C. waterbath until only a small ice chip remained. Cryovial contents were removed with a P1000 pipettor and delivered dropwise to a 15 mL conical tube containing 8 mL of warmed X-VIVO® 10 medium. The cell suspension was mixed gently using a 10 mL serological pipette. The cryovial was rinsed with 1 mL of X-VIVO® 10 medium and this was added to the tube.

The cells and solution were spun at room temperature in a benchtop centrifuge at 173 g (1,000 RPM in IEC Centra CL2 Centrifuge with Rotor 236 for 15 ml conical tubes) for 5 minutes. The supernatant was aspirated without disturbing the cell pellet. The cells were resuspended in 1 ml 37° C. X-VIVO® 10 medium.

A 10 uL sample of the cell suspension was removed for cell counting as described previously. Based on the live cell count, cells were seeded in the wells of the six-well plates at a density of 1.5×10$^5$ cells/cm2. Holding the plate inside the incubator, the plates were gently tilted back and forth at a 45° angle 15 times, then gently placed down on the shelf in the incubator and allowed to remain in place, as it is very important not to disturb the plate once it is placed on the shelf. The plates were incubated for 24-48 hours at 37° C./5% CO2 without disturbing.

24-48 hrs post-seeding, medium was changed and cells were photographed. Medium was replaced twice weekly. Passaged cells were assessed at 28-35 days post-seeding for morphological and genetic markers. Cells regained the distinct morphology of pigmented native RPE cells. Expression levels of RPE-65, BEST1, and TRYP1, markers of RPE phenotype, were comparable to those found in non-frozen RPE cells, demonstrating the ability of the methods described herein to preserve RPE viability and cell identity during extended cryopreservation.

Post-thaw viability, assessed by trypan blue staining 1 day after thaw, was 88%. Post-thaw recovery, measured as the percentage of thawed, live cells successfully recovered from the number of cells originally frozen in a cryovial (prior to plating) was 66%.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

The invention claimed is:

1. A method of producing RPE cells from pluripotent cells under xeno-free culture conditions, comprising
   (a) culturing pluripotent cells on a first xeno-free substrate in a xeno-free growth medium supplemented with one or more compositions which substantially maintains pluripotent cells in a pluripotent state, wherein the pluripotent cells are embryonic stem cells or induced pluripotent stem cells;
   (b) replacing the xeno-free growth medium with a xeno-free growth medium lacking any composition which maintains cells in a pluripotent state, wherein the cultured cells have not reached confluence at the time of such replacement of growth medium;
   (c) allowing the cultured cells on the first xeno-free substrate to undergo spontaneous differentiation, which results in some of the pluripotent cells differentiating into RPE cells;
   (d) treating the cultured cells on the first xeno-free substrate with a solution comprising a dissociation agent for a first interval of time, removing the solution comprising the dissociation agent, and immediately thereafter washing the first xeno-free substrate with buffer or medium;
   (e) physically separating cells other than mature RPE cells from the first xeno-free substrate;
   (f) treating the cultured cells remaining on the first xeno-free substrate with a solution comprising a dissociation agent for a second interval of time;
   (g) physically separating the mature RPE cells from the first xeno-free substrate to yield isolated RPE cells; and
   (h) culturing the isolated RPE cells on a second xeno-free substrate in xeno-free growth medium.

2. The method of claim 1, wherein
the dissociation agent is selected from the group consisting of trypsin, a trypsin-like enzyme, collagenase, dipsase, and EDTA.

3. The method of claim 1, wherein
the dissociation agent solution is a xeno-free composition.

4. The method of claim 1, wherein
the first time interval during which the cells are exposed to a solution comprising a dissociation agent does not exceed six minutes.

5. The method of claim 1, wherein
the buffer or medium is Dulbecco's Phosphate Buffered Saline.

6. The method of claim 1, wherein
the first xeno-free substrate and the second xeno-free substrate comprise a non-cellular substrate.

7. The method of claim 6, wherein
the non-cellular substrate is human or recombinant vitronectin.

8. The method of claim 6, wherein
the non-cellular substrate is parylene membrane coated with vitronectin, laminin, fibronectin, or peptides derived therefrom.

9. The method of claim 6, wherein
the non-cellular substrate is a vitronectin-derived peptide coated with laminin, fibronectin, or peptides derived therefrom.

10. The method of claim 1,
further comprising the step of adding antibiotics subsequent to washing the substrate with buffer or medium.

11. The method of claim 1,
further comprising the step of filtering a suspension of the isolated RPE cells subsequent to physically separating the mature RPE cells from the first xeno-free substrate.

12. The method of claim 1,
further comprising the step of quantifying a concentration of the mature RPE cells.

13. The method of claim 12, wherein
the quantification of the concentration of the mature RPE cells is accomplished using a cell counter with a gating diameter set between 6 µm and 20 µm.

14. The method of claim 1, wherein
the pluripotent cells are human cells.

15. The method of claim 1, wherein
the xeno-free growth media are MX-302 media or E8 media.

16. The method of claim 1, wherein
the one or more compositions which substantially maintains pluripotent cells in a pluripotent state is basic fibroblast growth factor.

17. The method of claim 16, wherein
the basic fibroblast growth factor is present in the xeno-free growth medium at a concentration between 50 µg/ml and 100 µg/ml.

18. The method of claim 1, wherein
the one or more compositions which substantially maintains pluripotent cells in a pluripotent state is transforming growth factor Beta-1.

19. The method of claim 18, wherein
the transforming growth factor Beta-1 is present in the xeno-free growth medium at a concentration between 0.1 ng/ml and 1 ng/ml.

* * * * *